United States Patent [19]

Dempski et al.

[11] Patent Number: 4,983,400

[45] Date of Patent: Jan. 8, 1991

[54] CONTROLLED RELEASE COMBINATION OF CARBIDOPA/LEVODOPA

[75] Inventors: Robert E. Dempski, Dresher; Edward C. Scholtz, King of Prussia; Donald W. Nibbelink, Lansdale; Scott A. Reines, New Hope, all of Pa.

[73] Assignee: Merck & Co., Inc., Rahway, N.J.

[21] Appl. No.: 444,222

[22] Filed: Dec. 1, 1989

Related U.S. Application Data

[60] Division of Ser. No. 315,057, Feb. 24, 1989, Pat. No. 4,900,755, which is a division of Ser. No. 223,861, Jul. 25, 1988, Pat. No. 4,832,957, which is a continuation-in-part of Ser. No. 131,601, Dec. 11, 1987, abandoned, which is a continuation-in-part of Ser. No. 874,988, Jun. 16, 1986, abandoned.

[51] Int. Cl.$^5$ .................. A61K 9/22; A61K 9/26; A61K 31/78

[52] U.S. Cl. .................... 424/469; 424/470; 424/486; 424/487; 424/81

[58] Field of Search ............... 424/469, 470, 81, 486, 424/487

[56] References Cited

U.S. PATENT DOCUMENTS

| | | | |
|---|---|---|---|
| Re. 29,892 | 1/1979 | Bayne | 514/565 |
| 3,961,041 | 6/1976 | Nishimura et al. | 424/466 |
| 3,995,058 | 11/1976 | Hammond et al. | 514/567 |
| 4,014,987 | 3/1977 | Heller et al. | 424/486 |
| 4,021,555 | 5/1977 | Seyfried et al. | 514/252 |
| 4,177,056 | 12/1979 | Mueller et al. | 424/81 |
| 4,190,672 | 2/1980 | Fahn | 514/566 |
| 4,304,591 | 12/1981 | Mueller et al. | 424/486 |
| 4,327,725 | 5/1982 | Cortese et al. | 424/473 |
| 4,329,356 | 5/1982 | Holland | 514/413 |
| 4,389,330 | 6/1983 | Tice et al. | 424/497 |
| 4,389,393 | 6/1983 | Schor et al. | 424/19 |
| 4,389,415 | 6/1983 | Scriabine | 514/565 |
| 4,413,012 | 11/1983 | Palfreyman et al. | 514/565 |
| 4,421,767 | 12/1983 | Palfreyman et al. | 514/567 |
| 4,423,099 | 12/1983 | Mueller et al. | 424/486 |
| 4,424,235 | 1/1984 | Sheth et al. | 514/567 |
| 4,440,740 | 4/1984 | Fix et al. | 514/772 |
| 4,446,138 | 5/1984 | Pack | 514/909 |
| 4,469,693 | 9/1984 | Bagli et al. | 514/255 |
| 4,469,694 | 9/1984 | Bagli et al. | 514/253 |
| 4,469,695 | 9/1984 | Bagli et al. | 514/255 |
| 4,497,826 | 2/1985 | Narabayashi et al. | 514/567 |
| 4,529,603 | 7/1985 | Mori et al. | 514/565 |
| 4,548,990 | 10/1985 | Mueller et al. | 424/486 |
| 4,606,909 | 8/1986 | Bechgaard et al. | 424/469 |
| 4,624,848 | 11/1986 | Lee | 424/486 |
| 4,685,918 | 8/1987 | Amidon et al. | 424/473 |
| 4,692,336 | 9/1987 | Eckenhoff et al. | 424/469 |
| 4,749,576 | 7/1988 | Lee | 424/486 |
| 4,783,337 | 11/1988 | Wong et al. | 424/469 |

(List continued on next page.)

FOREIGN PATENT DOCUMENTS

| | | |
|---|---|---|
| 36145 | 9/1981 | European Pat. Off. . |
| 147780 | 7/1985 | European Pat. Off. . |
| 237506 | 9/1987 | European Pat. Off. . |
| 252290 | 1/1988 | European Pat. Off. . |
| 253490 | 1/1988 | European Pat. Off. . |
| 260236 | 3/1988 | European Pat. Off. . |
| 290891 | 11/1988 | European Pat. Off. . |
| 320051 | 6/1989 | European Pat. Off. . |
| 324947 | 7/1989 | European Pat. Off. . |
| 3232873 | 3/1983 | Fed. Rep. of Germany . |

OTHER PUBLICATIONS

The Lancet, 781 (1973), Curzen et al.
The Lancet, 440 (1985), Juncos et al.
Neurology, 35, 201 (No. 6, No. 8) (1985).
Neurology, 36, 217 (No. 9) (1986).

Primary Examiner—Shep K. Rose
Attorney, Agent, or Firm—William H. Nicholson; Joseph F. DiPrima

[57] ABSTRACT

A matrix or monolithic drug delivery system for the controlled release of carbidopa and levodopa consists of the two drugs uniformly dispersed in a polymer vehicle at a concentration that is greater than the solubility of either drug in the polymer. Treatment of parkinsonism with the controlled release formulation provides several advantages over treatment with the standard carbidopa/levodopa combination presently employed.

3 Claims, 1 Drawing Sheet

U.S. PATENT DOCUMENTS

| | | | |
|---|---|---|---|
| 4,806,360 | 2/1989 | Leong et al. | 424/486 |
| 4,826,875 | 5/1989 | Chiese | 514/534 |
| 4,832,957 | 5/1989 | Dempski et al. | 424/469 |
| 4,840,799 | 6/1989 | Appelgren et al. | 424/473 |
| 4,844,984 | 7/1989 | Eckenhoff et al. | 424/473 |
| 4,851,228 | 7/1989 | Zentner et al. | 424/473 |
| 4,855,144 | 8/1989 | Leong et al. | 424/486 |
| 4,876,093 | 10/1989 | Theeuwes et al. | 424/469 |
| 4,883,666 | 11/1989 | Sabel et al. | 424/486 |
| 4,900,755 | 2/1990 | Dempski et al. | 424/469 |
| 4,938,967 | 7/1990 | Newton et al. | 424/469 |
| 4,940,465 | 7/1990 | Theeuwes et al. | 424/469 |

CONTROLLED RELEASE COMBINATION OF CARBIDOPA/LEVODOPA

This is a division of Ser. No. 07/315,057, filed Feb. 24, 1989 (now U.S. Pat. No. 4,900,755), which in turn was a division of Ser. No. 07/223,861, filed July 25, 1988 (now U.S. Pat. No. 4,832,957), which in turn was a continuation-in-part of Ser. No. 07/131,601, filed Dec. 11, 1987 (now abandoned), which was a continuation-in-part of Ser. No. 06/874,988, filed June 16, 1986 (now abandoned).

BACKGROUND OF THE INVENTION

This invention is concerned with a controlled release formulation for the simultaneous delivery of levodopa and carbidopa in the treatment of parkinsonism whereby the adverse reactions and inadequacies often experienced with the administration of standard carbidopa/levodopa combinations are minimized.

SINEMET ® (Merck & Co. Inc., Rahway, N.J.) is the registered trademark for a therapeutic agent useful in the treatment of idiopathic Parkinsonism. It is a combination of levodopa and carbidopa and is provided in tablets of 10 mg carbidopa/100 mg of levodopa; 25 mg of carbidopa/250 mg of levodopa; and 25 mg of carbidopa/100 mg of levodopa. The usual dose is 3 to 4 tablets daily.

Before SINEMET was introduced to the market in 1975, parkinsonism was treated with levodopa by itself. Large doses of levodopa were necessary to adequately control the Parkinson syndrome and severe adverse reactions, especially emesis, were experienced. To minimize these adverse reactions attempts were made to deliver levodopa in a sustained release fashion. In fact there was a product called Brocadopa Temtabs. Several studies failed to show any advantage of the sustained release formulation over a standard preparation. See Eckstein et al., *The Lancet*, Feb. 24, 1973, page 431 which states at 432, "for the majority of parkinsonians in our study sustained-release levodopa offered no definite advantage over a standard preparation". Also curzon et al., *The Lancet*, Apr. 7, 1973, page 781, states, "These results suggest there is no practical advantage to be gained by the use of an oral sustained-release preparation of levodopa".

Therapy with SINEMET is widely accepted as the cornerstone in treating idiopathic Parkinson's disease. However, "wearing-off" and "on-off" phenomena have emerged as major problems in the long-term treatment of Parkinson's disease. After two to three years, many patients begin to experience oscillating motor fluctuations which become increasingly disabling. The essential feature is a change from mobility to immobility, which may occur many times a day. Predictable waning of therapeutic effects, following each dose of SINEMET, is known as "wearing-off" and may first occur during stage II-III of the disease. Such response fluctuations occur in 15 to 40% of patients after two to three years of treatment, and in a greater percentage with longer duration of illness. The fluctuations in levodopa levels which accompany SINEMET treatment may in themselves contribute to the development of clinical oscillations.

The clinical manifestations of "on-off" include rapid and unpredictable swings from mobility to immobility. "On" periods can usually be correlated with high or rising plasma levodopa levels and are often associated with distinct, abnormal involuntary movements (dose-related dyskinesias), while "off" periods are commonly but not invariably associated with low or falling plasma-levodopa levels. The relation of "off" periods to low plasma levodopa levels and the observation that the administration of apomorphine during an "off" period may restore function suggests that most such periods are due to cerebral dopamine deficiency. Frequent dosage administration helps to alleviate oscillating clinical responses but dyskinesias and bradykinetic episodes may still occur.

Intravenous levodopa has been used to provide stable plasma levels of 2000 to 5000 ng/ml in advanced parkinsonian patients. This procedure reduces motor oscillations, but optimal response in some patients still include either tremor and bradykinesia or mobility with dyskinesia. High protein meals cause a decline in response without affecting plasma levodopa levels, presumably by inhibiting transport of levodopa into the brain.

The above considerations indicate that a dosage preparation of SINEMET possessing less rapid dissolution properties and providing a more even plasma level profile of levodopa should be efficacious in alleviating some but not all oscillating therapeutic responses.

If the development of clinical fluctuations is promoted by oscillating levodopa levels, a controlled release preparation may also help to prevent the emergence of "wearing-off" and "on-off" phenomena.

Now, with the present invention there is provided a controlled release form of the combination of carbidopa/levodopa designed to obviate or at least alleviate problems associated with the standard combination therapy. Dyskinesias and other central nervous system side effects, and gastrointestinal side effects may be reduced in patients sensitive to high plasma levodopa levels. Patients with oscillating symptoms should respond to the more constant plasma levodopa levels with a more even clinical response. Furthermore, controlled release SINEMET is expected to represent a more convenient dosage form (i.e., allowing for less frequent medication) for many patients who require standard SINEMET four or more times a day. A twice-daily dosage regimen may also be feasible in some patients.

DETAILED DESCRIPTION OF THE INVENTION

The novel controlled release tablet of carbidopa/levodopa of this invention is a matrix or monolithic drug delivery system containing carbidopa and levodopa as active ingredients. The system consists of the two drugs, uniformly dispersed in a polymer vehicle at a concentration that is greater than either drug solubility in the polymer vehicle which is either a single or a combination of polymers.

The novel delivery system provides slow release of both drug components either by erosion or by a diffusion controlled mechanism, depending on the particular polymer vehicle.

Release of drug by erosion occurs by slow disintegration of the tablet surface. Release of drug by diffusion occurs either through the space between the macromolecular polymer chains or through a porous network filled with aqueous medium. Optimum erosion or diffusion conditions can be achieved by controlling the crystalline phase porous structure, degree of swelling, polymer type, polymer ratio, drug concentration and other salient parameters.

Figure 1:
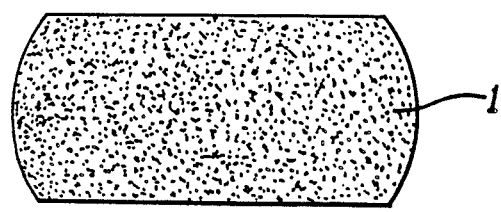
FIG. 1, is a cross-section of a tablet-shaped homogeneous polymer matrix showing the drug components, 1, homogeneously dispersed in the matrix.
Figure 2:
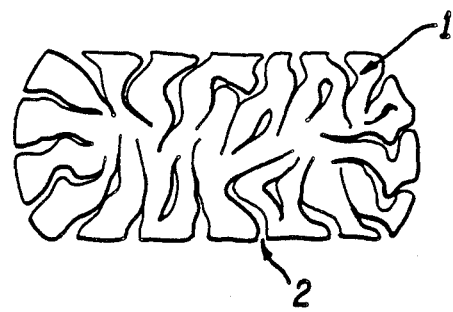
FIG. 2, is a schematic representation of the same polymer matrix, 1, after some of the drug has been delivered by diffusion by entry of liquids into the tortuous microporous channels, 2, followed by exit of drug solution through the same tortuous path. This matrix remains essentially intact while delivering its drug content.
Figure 3:
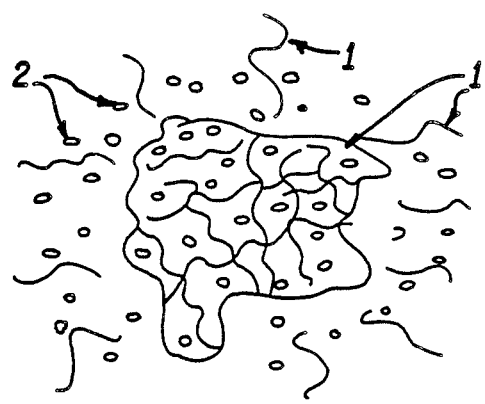
FIG. 3 is a cross-section of a schematic representation of the polymer matrix, 1, after some of the drug has been delivered by erosion by liquids whereby polymer, 1, and active ingredients, 2, are dispersed in the, fluid as solute or suspensoid.
Figure 3A:
FIG. 3a, is a schematic representation of the polymer matrix, 1, after essentially all of the drug, 2, has been delivered by erosion. This matrix completely disintegrates while delivering its drug content.

The polymer vehicle is a mono-polymer or copolymer or combinations thereof and are selected from: water soluble polymers such as hydroxypropyl cellulose, hydroxypropylmethyl cellulose, polyvinyl pyrrolidone, polyethylene glycol, starch, methyl cellulose; and less water-soluble polymers such as polyvinyl acetate-crotonic acid copolymer; polyvinyl chloride, polyethylene, cellulose acetate, polyvinyl alcohol, ethylene vinyl acetate copolymer, polyvinyl acetate, polymethyl methacrylate, ethyl cellulose and the like. The preferred vehicle is a combination of the water soluble polymer, hydroxypropyl cellulose and the less water soluble copolymer of polyvinyl acetate-crotonic acid.

Other components of the novel formulation are optional dyes and tablet lubricants such as: metallic salts of acids including aluminum stearate, calcium stearate, magnesium stearate, sodium stearate, and zinc stearate; fatty acids, hydrocarbons and fatty alcohols including stearic acid, palmitic acid, liquid paraffin, stearyl alcohol, and palmityl alcohol; fatty acid esters including glyceryl monostearate, glyceryl (mono- and di-) stearate, triglycerides, glyceryl (palmitic-stearic) ester, sorbitan monostearate, saccharose monostearate, saccharose monopalmitate, and sodium stearyl fumarate; alkyl sulfates, including sodium lauryl sulfate, and magnesium lauryl sulfate; polymers including polyethylene glycols, polyoxyethylene glycols, and polytetrafluoroethylene (Teflon); and inorganic materials such as talc. The preferred tablet lubricant is magnesium stearate.

In a typical formulation the components thereof are present in the following quantities:

| Component | Quantity Range | Preferred Range |
|---|---|---|
| Levodopa | 20–1200 mg[1] | 100–400 mg |
| Carbidopa | 5–300 mg[1] | 25–100 mg |
| Water Soluble Polymer | 0–120 mg[2] | 5–25 mg |
| less water soluble polymer | 0–120 mg[2] | 2–50 mg |
| lubricant | 0–25 mg | 1–10 mg |

[1]The relative amounts of carbidopa to levodopa are preferably from about 1 carbidopa/10 levodopa to 1 carbidopa/4 levodopa.
[2]In a given formulation both polymers cannot be 0 mg.

A process for preparing the novel formulations comprises mixing levodopa, carbidopa and colorants with a hydroalcoholic or other suitable solvent dispersion of the polymers(s), drying, milling, mixing with the lubricant and compressing into tablets.

Alternatively the formulation can be prepared by mixing levodopa, carbidopa and colorants and adding hydroxypropylcellulose and/or polyvinyl acetate/crotonic acid copolymer, either dry or dispersed in a solvent such as water, alcohol or hydroalcohol. The mixture is dried, mixed with lubricant and compressed into tablets.

Specific examples of the novel controlled release formulation of this invention are as follows:

EXAMPLE 1

| Ingredient | Per Tablet |
|---|---|
| Levodopa USP | 200 mg |
| Carbidopa Hydrous USP | 54 mg |
| Cellulose Acetate | 50 mg |
| Magnesium Stearate Impalpable Powder NF | 5.5 mg |
| FD & C Blue No. 1 | 1.0 mg |

EXAMPLE 2

| Ingredient | Per Tablet |
|---|---|
| Levodopa USP | 200 mg |
| Carbidopa Hydrous USP | 54 mg |
| Vinyl Acetate/Crotonic Acid Copolymer[1] | 6.5 mg |
| Hydroxypropyl Cellulose NF[2] | 17.0 mg |
| Magnesium Stearate Impalpable Powder NF | 3.0 mg |
| Red 347 Mapico | 0.4 mg |
| Yellow D & C No. 10 Aluminum Lake HT | 1.0 mg |

[1]Vinac ASB-516 ® containing about 5% crotonic acid; molar viscosity 15–17 cps; molecular weight 95,000; available from Air Products and Chemicals, Inc., Box 538, Allentown, PA 18105, U.S.A.
[2]Klucel LF ®, molecular weight, 75,000; viscosity of 5% aqueous solution 75–150 cps; available from Hercules, Incorporated, Wilmington, Delaware, 19894, U.S.A.

EXAMPLE 3

| Ingredient | Per Tablet |
|---|---|
| Levodopa USP | 200 mg |
| Carbidopa Hydrous USP | 54 mg |
| Carboxyvinyl Polymer | 60 mg |
| Microcrystalline Cellulose | 20 mg |
| Magnesium Stearate Impalpable Powder NF | 5.5 mg |
| FD & C Red No. 3 | 1.0 mg |

EXAMPLE 4

| Ingredient | Per Tablet | |
|---|---|---|
| Levodopa USP | 200 mg | 100 mg. |
| Carbidopa Hydrous USP | 54 mg | 27 mg. |
| Vinyl Acetate/Crotonic Acid Copolymer[1] | 5.0 mg | 2.5 mg |
| Hydroxypropyl Cellulose NF[2] | 17.0 mg | 8.5 mg |
| Magnesium Stearate Impalpable Powder NF | 3.0 mg | 1.5 mg. |
| Red 347 Mapico | 0.3 mg | 0.15 mg. |
| Yellow D & C No. 10 Aluminum Lake HT | 1.1 mg | 0.55 |

[1]See footnote, Example 2.
[2]See footnote, Example 2.

EXAMPLE 5

| Ingredient | Per Tablet |
|---|---|
| Levodopa USP | 200 mg |
| Carbidopa Hydrous USP | 54 mg |

EXAMPLE 5-continued

| Ingredient | Per Tablet |
| --- | --- |
| Hydroxypropyl Cellulose NF[1] | 90 mg |
| Magnesium Stearate Impalpable Powder NF | 8.0 mg |
| Red 347 Mapico | 0.4 mg |
| Yellow D & C No. 10 Aluminum Lake HT | 1.0 mg |

[1]See footnote (2), Example 2.

EXAMPLE 6

| Ingredient | Per Tablet |
| --- | --- |
| Levodopa USP | 400 mg |
| Carbidopa Hydrous USP | 108 mg |
| Polymethyl Methacrylate | 120.0 mg |
| Magnesium Stearate Impalpable Powder NF | 5.5 mg |
| FD & C Red No. 3 | 0.4 mg |
| Yellow D & C No. 10 Aluminum Lake HT | 1.0 mg |

EXAMPLE 7

| Ingredient | Per Tablet |
| --- | --- |
| Levodopa USP | 100 mg |
| Carbidopa Hydrous USP | 54 mg |
| Ethyl Cellulose | 20.0 mg |
| Methyl Cellulose | 5.0 mg |
| Magnesium Stearate Impalpable Powder NF | 5.5 mg |
| FD & C Red No. 3 | 0.4 mg |
| Yellow D & C No. 10 Aluminum Lake HT | 1.0 mg |

Two controlled release formulations, No. 1 and No. 2 were compared to standard SINEMET in 20 patients with uncomplicated Parkinson's disease. Mean disability scores were similar over two weeks in patients who received No. 1 or standard SINEMET and in patients who received No. 2 or standard SINEMET. (Because of the design of this study, the group of 10 patients which received No. 1 was different from the 10 patients who received No. 2; however, all patients received standard SINEMET).

| Ingredient | Per Tablet (mg) | |
| --- | --- | --- |
| | No. 1 CR-2 | No. 2 CR-3 |
| Levodopa | 100 | 200 |
| Carbidopa | 50 | 50 |
| Polyvinyl acetate-Crotonic acid Co-polymer[1] | 3 | 20 |
| Magnesium Stearate | 1.7 | 5.5 |
| Hydroxypropyl Cellulose NF[2] | 10 | — |

[1]See footnote, Example 2.
[2]See footnote, Example 2.

The pharmacokinetic profiles of the sustained release formulations were clearly different from that of standard SINEMET Patients on No. 1 achieved peak plasma levodopa concentrations 2.8±1.2 hours after dosing, compared to a $T_{max}$ of 1.1±0.33 hours with standard SINEMET. For the No. 2 preparation $T_{max}$ was 3.1±2.2 hours, compared to 1.4±0.5 hours with standard SINEMET. The eight hour bioavailabilities of No. 1 and No. 2 relative to standard SINEMET were estimated to be 86% and 75%, respectively.

Although mean peak plasma levodopa concentrations for No. 1 and No. 2 were only about half of those produced by SINEMET, and the 8 hour levels following No. 1 or No. 2 administration exceeded those with SINEMET, indicating sustained release properties for both CR formulations.

Based on these results, and the preferable 1:4 ratio of the No. 2 tablet, four open-label clinical and pharmacokinetic studies of No. 2 were conducted in parkinsonian patients with motor fluctuations. Among 30 such patients (22 with "wearing off" and 8 with unpredictable "on/off"), only a few showed marked improvement with decreased "off" time and smooth response during the day. Many others benefited from nighttime improvement including better sleep and mobility, and improved early morning function. Sustained elevated plasma levodopa levels were achieved, but were associated with unpredictable variability.

The No. 2 formulation proved to be extremely difficult to use because of a marked delay in onset of response after each dosage, a requirement for very high daily dosages (150-400% of standard SINEMET), and very poor correlation between time of dose and rise in plasma levodopa levels. In fact, nighttime and early morning plasma levels were sometimes higher than daytime levels, although dosing occurred throughout the day and not at night. Severe, sustained, and unpredictable periods of dyskinesias and similarly sustained "off" periods were observed. B.I.D. dosage administration was unsuccessful in 9 of 9 patients with mild to moderate fluctuations. Formulation No. 2 had to be given nearly as frequently a standard SINEMET in most patients.

The results of these studies strongly indicated that the release rate and bioavailability of the No. 2 tablet were too low in vivo, and probably very sensitive to effects of food and gastric pH. It appeared that in many patients much of the daytime dosage was stored in the stomach and not released until nighttime. A fragmentable matrix with more rapid dissolution characteristics, such as No. 1, had the potential to eliminate some of these problems.

These considerations led to the development of the No. 3 formulation. (Example 4) which has the same in vivo dissolution properties and polymeric matrix as No. 1 but contains 50 mg of carbidopa and 200 mg of levodopa. Fifty patients were enrolled in the No. 3 studies, and preliminary clinical and/or pharmacokinetic data are available from approximately 40 of them.

All four investigators consider the No. 3 formulation to be much easier to use than No. 2, due to (1) predictable onset of response (2) dosage requirements which are comparable to or slightly higher than standard SINEMET, and (3) more sustained therapeutic action during the day. Most patients who have completed the initial phase of the No. 3 trails requested long-term treatment because of clinical improvement. In general, dosing frequency can be reduced 25-50% with No. 3 relative to standard SINEMET. Clinical fluctuations are reduced throughout the day and occasionally eliminated. Patients with mild to moderate fluctuations (especially end-of-dose "wearing-off") benefit most, although half of the more severe patients have also improved. Pharmacokinetic data indicate that plasma levodopa levels are sustained for 3-6 hours following a dose of No. 3, as compared to 1-2 hours with standard SINEMET.

Onset of response after a single dose of No. 3 is less rapid than with standard SINEMET and may require 45 minutes. In patients with advanced disease, nighttime and early-morning response with No. 3 is better than with standard SINEMET but notably less than with No. 2. Plasma L-DOPA levels correlate well with these observations in that early morning L- DOPA levels are moderately higher with No. 3 than standard SINEMET but much less than with No. 2.

Dyskinesia, mental confusion and psychosis have been observed at higher doses in patients who had similar side effects with standard SINEMET. Sustained dyskinesias or "off" periods have not been significant problems to date.

Another formulation (Example 2) with dissolution properties intermediate to those of No. 2 and No. 3 has also been developed. This formulation will provide nighttime benefits in severe patients over those seen with No. 3.

We claim:

1. A controlled release solid oral dosage formulation consisting essentially of a uniform dispersion of 5-300 mg of carbidopa, 20-1200 mg of levodopa in a polymer vehicle of 2 to 120 mg of polymethyl methacrylate, whereby following administration the carbidopa and levodopa are released slowly and simultaneously from the formulation.

2. The controlled release solid oral dosage formulation of claim 1 consisting essentially of a uniform dispersion of 25-100 mg of carbipopa, 100-400 mg of levodopa, in a polymer vehicle of 2 to 120 mg of polymethyl methacrylate, whereby following administration the carbidopa and levodopa are released slowly and simultaneously from the formulation.

3. The formulation of claim 1 comprising 400 mg of levodopa, 100 mg of carbidopa and 120 mg of polymethyl methacrylate.

* * * * *